United States Patent
Brisson

(10) Patent No.: US 12,419,698 B2
(45) Date of Patent: *Sep. 23, 2025

(54) SYSTEM AND METHOD OF DISPLAYING IMAGES FROM IMAGING DEVICES

(71) Applicant: INTUITIVE SURGICAL OPERATIONS, INC., Sunnyvale, CA (US)

(72) Inventor: Gabriel F. Brisson, Livermore, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/646,112

(22) Filed: Apr. 25, 2024

(65) Prior Publication Data

US 2024/0268899 A1  Aug. 15, 2024

Related U.S. Application Data

(63) Continuation of application No. 17/265,486, filed as application No. PCT/US2019/044852 on Aug. 2, 2019, now Pat. No. 11,992,273.

(Continued)

(51) Int. Cl.
*A61B 34/20* (2016.01)
*A61B 1/00* (2006.01)
*A61B 90/00* (2016.01)

(52) U.S. Cl.
CPC .......... *A61B 34/20* (2016.02); *A61B 1/00193* (2013.01); *A61B 90/37* (2016.02);
(Continued)

(58) Field of Classification Search
CPC ........ A61B 1/00193; A61B 2034/2048; A61B 2034/2055; A61B 2090/376;
(Continued)

(56) References Cited

U.S. PATENT DOCUMENTS 5,876,325 A  3/1999  Mizuno et al.
6,424,885 B1  7/2002  Niemeyer et al.
(Continued)

FOREIGN PATENT DOCUMENTS

WO  WO-2015142796 A1  9/2015
WO  WO-2015171614 A1  11/2015

OTHER PUBLICATIONS

Yi Ren,"Faster Feedback for Remote Scene Viewing with Pan-Tilt Stereo Camera," Jul. 7, 2016, IEEE Virtual Reality Conference 2016,pp. 273-274.*

(Continued)

*Primary Examiner* — Omar S Ismail
(74) *Attorney, Agent, or Firm* — Artegis Law Group, LLC—Intuitive Surgical

(57) ABSTRACT

Techniques for displaying images from an imaging device include a display device and one or more processors coupled to the display device. The one or more processors are configured to track movement of an imaging device, determine a display-device-to-imaging-window transform based on the tracked movement of the imaging device, and display an image from the imaging device on the display device. A position and an orientation of the image on the display device is based on the display-device-to-imaging-window transform. The position and the orientation of the image on the display device provides one or more cues to an operator regarding at least one of: an inability of the imaging device to follow a command to move the imaging device, a range of motion limit of the imaging device, or a mismatch in (Continued)

degrees of freedom between the imaging device and the display device.

20 Claims, 4 Drawing Sheets

Related U.S. Application Data

(60) Provisional application No. 62/714,326, filed on Aug. 3, 2018.

(52) U.S. Cl.
CPC .............. *A61B 2034/2048* (2016.02); *A61B 2034/2055* (2016.02); *A61B 2090/376* (2016.02); *A61B 2090/378* (2016.02)

(58) Field of Classification Search
CPC ... A61B 2090/378; A61B 34/20; A61B 34/30; A61B 90/37; G09G 2340/0464; G09G 2354/00; G09G 5/00; H04N 13/204; H04N 13/344
See application file for complete search history.

(56) References Cited

U.S. PATENT DOCUMENTS

| | | | | |
|---|---|---|---|---|
| 8,060,279 | B2* | 11/2011 | Stuetzler | B60R 21/0133 180/282 |
| 8,808,164 | B2 | 8/2014 | Hoffman et al. | |
| 10,265,057 | B2 | 4/2019 | Herzlinger et al. | |
| 11,992,273 | B2* | 5/2024 | Brisson | G09G 5/00 |
| 2009/0177358 | A1* | 7/2009 | Stuetzler | B60R 21/0133 701/45 |
| 2010/0256558 | A1* | 10/2010 | Olson | A61B 34/77 604/95.01 |
| 2011/0107270 | A1* | 5/2011 | Wang | G16H 20/40 703/11 |
| 2011/0273466 | A1* | 11/2011 | Imai | G09G 3/20 345/589 |
| 2011/0298937 | A1* | 12/2011 | Ogawa | H04N 23/6812 348/208.4 |
| 2014/0005555 | A1* | 1/2014 | Tesar | A61B 1/0004 600/476 |
| 2014/0071580 | A1* | 3/2014 | Higginson | H02N 13/00 361/234 |
| 2014/0148808 | A1* | 5/2014 | Inkpen | A61B 90/06 73/866.5 |
| 2014/0276001 | A1* | 9/2014 | Ungi | A61B 5/064 600/424 |
| 2015/0018622 | A1* | 1/2015 | Tesar | A61B 50/13 600/202 |
| 2015/0109187 | A1* | 4/2015 | Maeda | G06F 3/14 345/8 |
| 2016/0041630 | A1* | 2/2016 | Hosenpud | G06F 3/03545 345/157 |
| 2016/0100107 | A1* | 4/2016 | Nakamura | H04N 5/77 348/77 |
| 2016/0112680 | A1* | 4/2016 | Nakamura | H04N 5/77 348/143 |
| 2017/0097802 | A1* | 4/2017 | Jeong | G06F 3/1423 |
| 2017/0140539 | A1* | 5/2017 | Wang | B25J 9/1697 |
| 2017/0235380 | A1* | 8/2017 | Sendai | G06F 3/0346 345/173 |
| 2017/0372640 | A1* | 12/2017 | Lampotang | G09B 9/00 |
| 2018/0368656 | A1* | 12/2018 | Austin | A61B 1/24 |
| 2019/0090728 | A1* | 3/2019 | Fanenbruck | A61B 1/05 |
| 2020/0261160 | A1 | 8/2020 | Peine et al. | |
| 2021/0315643 | A1 | 10/2021 | Brisson | |

OTHER PUBLICATIONS

Tobias Sielhorst,"Advanced Medical Displays: A Literature Review of Augmented Reality," Nov. 19, 2008, Journal of Display Technology, vol. 4, No. 4, Dec. 2008,pp. 451-462.*

Hongen Liao,"3-D Augmented Reality for MRI-Guided Surgery Using Integral Videography Autostereoscopic Image Overlay," May 14, 2010, IEEE Transactions on Biomedical Engineering, vol. 57, No. 6, Jun. 2010,pp. 1476-1484.*

Jens Grubert,"A Survey of Calibration Methods for Optical See-Through Head-Mounted Displays," Jul. 27, 2018, IEEE Transactions on Visualization and Computer Graphics, vol. 24, No. 9, Sep. 2018,pp. 2649-2655.*

Hongen Liao,"Surgical Navigation by Autostereoscopic Image Overlay of Integral Videography," Dec. 12, 2003, IEEE Transactions on Information Technology in Biomedicine, vol. 8, No. 2, Jun. 2004,pp. 114-118.*

Zhenyuan Deng,"Predictive Display System for Tele-manipulation using Image-Based Modeling and Rendering," Jan. 7, 2004, Proceedings of the 2003 IEEE/RSJ Intl. Conference on Intelligent Robots and Systems Las Vegas, Nevada ,Oct. 2023,pp. 2797-2802.*

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.*

Wu C., et al., "Drone Streaming with Wi-Fi Grid Aggregation for Virtual Tour," arxiv.org, Cornell University Library, 201 Olin Library Cornell University Ithaca, NY 14853, May 31, 2016, XP080965502, 2 pages.*

Deng Z., et al., "Predictive Display System for Tele-manipulation Using Image-Based Modeling and Rendering," IEEE/RSJ International Conference on Intelligent Robots and Systems(IROS), Oct. 2003, pp. 2797-2802.

Grubert J., et al., "A Survey of Calibration Methods for Optical See-through Head-mounted Displays," IEEE Transactions on Visualization and Computer Graphics, Sep. 2018, vol. 24(9), pp. 2649-2662.

International Preliminary Report on Patentability for Application No. PCT/2019/044852, mailed on Feb. 18, 2021, 12 pages.

International Search Report and Written Opinion for Application No. PCT/US2019/044852, mailed on Oct. 24, 2019, 15 pages.

Liao H., et al., "3-D Augmented Reality for MRI-Guided Surgery Using Integral Videography Autostereoscopic Image Overlay," IEEE Transactions on Biomedical Engineering, Jun. 2010, vol. 57(6), pp. 1476-1486.

Liao H., et al., "Surgical Navigation by Autostereoscopic Image Overlay of Integral Videography," IEEE Transactions on Information Technology in Biomedicine, Jun. 2004, vol. 8(2), pp. 114-121.

Ren Y., et al., "Faster Feedback for Remote Scene Viewing with Pan-Tilt Stereo Camera," IEEE Virtual Reality Conference, Mar. 2016, pp. 273-274.

Sielhorst T., et al., "Advanced Medical Displays: A Literature Review of Augmented Reality," Journal of Display Technology, IEEE SErvice Center, New York, NY, US, vol. 4, No. 4, Dec. 1, 2008, pp. 451-467.

\* cited by examiner

SYSTEM AND METHOD OF DISPLAYING IMAGES FROM IMAGING DEVICES

CROSS-REFERENCE TO RELATED APPLICATIONS

This application is a continuation of U.S. patent application Ser. No. 17/265,486, filed Feb. 2, 2021, which is a U.S. National Stage Patent application of International Patent Application No. PCT/US2019/044852, filed Aug. 2, 2019, the benefit of which is claimed, and claims priority to and benefit of U.S. Provisional Patent Application No. 62/714,326, filed Aug. 3, 2018, entitled "System and Method of Displaying Images from Imaging Devices." Each of these related applications is incorporated herein by reference.

TECHNICAL FIELD

The present disclosure relates generally to control of devices with repositionable imaging devices and more particularly to displaying images from the imaging devices.

BACKGROUND

More and more devices are being replaced with computer-assisted electronic devices. This is especially true in industrial, entertainment, educational, and other settings. As a medical example, the hospitals of today with large arrays of electronic devices being found in operating rooms, interventional suites, intensive care wards, emergency rooms, and/or the like. For example, glass and mercury thermometers are being replaced with electronic thermometers, intravenous drip lines now include electronic monitors and flow regulators, and traditional hand-held surgical and other medical instruments are being replaced by computer-assisted medical devices.

These electronic devices provide both advantages and challenges to the personnel operating them. Many of these electronic devices may be capable of autonomous or semi-autonomous motion of one or more repositionable arms and/or end effectors. It is also common for personnel to control the electronic devices using one or more input devices located at a user control system to control the motion and/or operation of the repositionable arms and/or the end effectors. When the electronic device is operated remotely from the user control system and there is a discrepancy between a command to the electronic device issued by the operator, and the electronic device's execution of the command, the operator or other personnel may have incomplete or inaccurate perceptions of electronic device operation. Providing the operator or other personnel with appropriate feedback would help improve the usability and intuitive operation of the electronic device. As a specific example, providing feedback about imaging devices that provide images to operators or other personnel can aid accurate use of the imaging devices and any other devices used with the imaging devices.

Accordingly, improved methods and systems for providing feedback from electronic devices, including for those associated with imaging devices, are desirable.

SUMMARY

Consistent with some embodiments, a computer-assisted device includes a display device and one or more processors coupled to the display device. The one or more processors are configured to track movement of an imaging device, determine a display-device-to-imaging-window transform based on the tracked movement of the imaging device and a corresponding command to move the imaging device, and render an image received from the imaging device on the display device at a position and orientation on the display device based on the display-device-to-imaging-window transform.

Consistent with some embodiments, a method includes tracking movement of an imaging device, determining a display-device-to-imaging-window transform based on the tracked movement of the imaging device and a corresponding command to move the imaging device, and rendering an image received from the imaging device on a display device of a computer-assisted device at a position and orientation on the display device based on the display-device-to-imaging-window transform.

Consistent with some embodiments, a non-transitory machine-readable medium includes a plurality of machine-readable instructions which when executed by one or more processors are adapted to cause the one or more processors to perform any of the methods described herein.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

Figure 1:
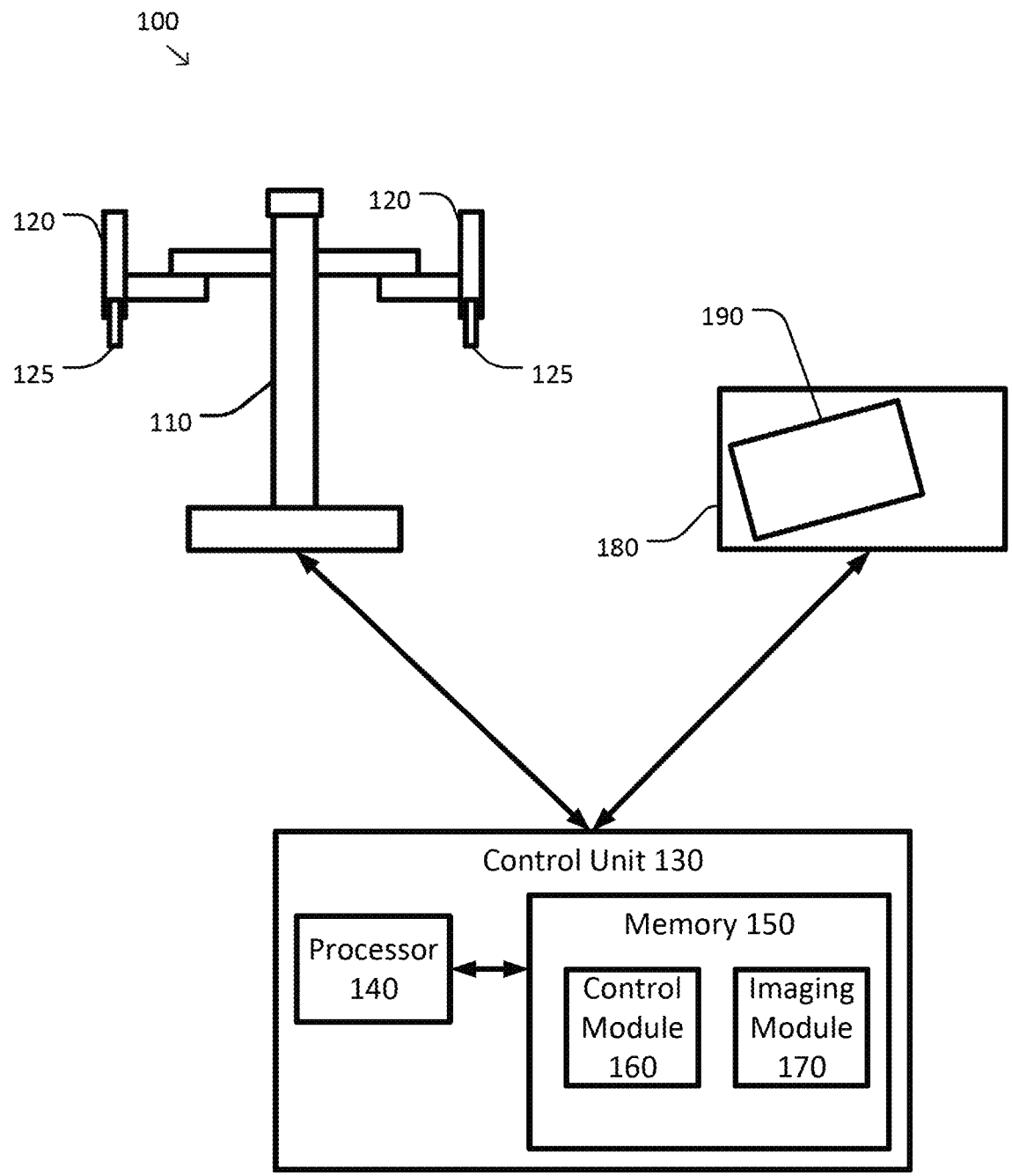
FIG. 1 is a simplified diagram of a computer-assisted system according to some embodiments.

In the figures, elements having the same designations have the same or similar functions.

DETAILED DESCRIPTION

This description and the accompanying drawings that illustrate inventive aspects, embodiments, implementations, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of computer-assisted devices and elements in terms of their state in three-dimensional space. As used herein, the term "position" refers to the location of an element or a portion of an element in a three-dimensional space (e.g., three degrees of translational freedom along Cartesian x-, y-, and z-coordinates). As used herein, the term "orientation" refers to the rotational placement of an element or a portion of an element (three degrees of rotational freedom—e.g., roll, pitch, and yaw). As used herein, the term "shape" refers to a set positions or orientations measured along an element. As used herein, and for a device with repositionable arms, the term "proximal" refers to a direction toward the base of the computer-assisted device along its kinematic chain and "distal" refers to a direction away from the base along the kinematic chain.

Aspects of this disclosure are described in reference to computer-assisted systems and devices, which may include systems and devices that are teleoperated, remote-controlled, autonomous, semiautonomous, robotic, and/or the like. Further, aspects of this disclosure are described in terms of an implementation using a surgical system, such as the da Vinci® Surgical System commercialized by Intuitive Surgical, Inc. of Sunnyvale, California. Knowledgeable persons will understand, however, that inventive aspects disclosed herein may be embodied and implemented in various ways, including robotic and, if applicable, non-robotic embodiments and implementations. Implementations on da Vinci® Surgical Systems are merely exemplary and are not to be considered as limiting the scope of the inventive aspects disclosed herein. For example, techniques described with reference to surgical instruments and surgical methods may be used in other contexts. Thus, the instruments, systems, and methods described herein may be used for humans, animals, portions of human or animal anatomy, industrial systems, general robotic, or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

FIG. 1 is a simplified diagram of a computer-assisted system 100 according to some embodiments. As shown in FIG. 1, computer-assisted system 100 includes a device 110 with one or more repositionable arms 120. Each of the one or more repositionable arms 120 may support one or more end effectors 125. In some examples, device 110 may be consistent with a computer-assisted surgical device. The one or more end effectors 125 may include instruments, imaging devices, and/or the like. In some medical examples, the instruments may include medical instruments, such as clamps, grippers, retractors, cautery tools, suction tools, suturing devices, and/or the like. In some medical examples, the imaging devices may include endoscopes, cameras, ultrasonic devices, fluoroscopic devices, and/or the like. In some examples, each of the one or more end effectors 125 may be inserted into a worksite (e.g., anatomy of a patient, a veterinary subject, and/or the like) through a respective cannula mounted to a respective one of the one or more repositionable arms 120. In some examples, a direction of view of an imaging device may correspond to an insertion axis of the imaging device and/or may be at an angle relative to the insertion axis of the imaging device. In some examples, a field of view of the imaging device may not be aligned with the roll and/or pitch degrees of freedom of a shaft coupling the imaging device to a corresponding one of the one or more repositionable arms 120. In some examples, input control mechanisms used to manipulate the imaging device may not include a one-for-one match between degrees of freedom of the imaging device.

Device 110 is coupled to a control unit 130 via an interface. The interface may include one or more cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), graphics processing units (GPUs) and/or the like in control unit 130. Control unit 130 may be implemented as a stand-alone subsystem and/or as a board added to a computing device or as a virtual machine.

Memory 150 may be used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 150 includes a control module 160 that may be used to control and/or track the position and/or orientation of an imaging device (e.g., one of the one or more end effectors 125) of device 110 and an imaging module 170 that may be used to receive images from the imaging device and display them on a display device 180 as is described in further detail below. And although FIG. 1 shows control module 160 and imaging module 170 in a same memory 150 of a same control unit 130, control module 160 and imaging module 170 may alternatively be associated with different control units.

Control unit 130 is further coupled to display device 180 via the interface. In some examples, display device 180 may be a repositionable display device, such as an adjustable monitor, a tablet, a smart phone, a head-mounted display, and/or the like. Display device 180 may be used by computer-assisted system 100 and imaging module 170 to display one or more images from the imaging device in an imaging window 190 rendered on display device 180. In some examples, a position, size, aspect ratio, orientation, and/or the like of imaging window 190 may be controlled by an operator.

According to some embodiments, different arrangements and approaches may be used to control the position and/or orientation of the imaging device. In some examples, when display device 180 is a head-mounted display, movement and/or reorientation of the operator's head may be tracked and used to generate movement commands for the imaging device. As an example, when the operator's head is rotated to the left and/or the operator's torso is rotated to the left and the head-mounted display moves accordingly, the direction of view of the imaging device may be panned left. In some examples, when display device 180 is hand-held, motion of display device 180 may be used to control the position and/or orientation of the imaging device (e.g., via teleoperation). As an example, when display device 180 is moved upward, a field of view of the imaging device may be moved upward via a corresponding movement of the imaging device. In some examples, position and/or orientation of the imaging device may be controlled independently of display device 180, such as by tracking one or more hands of the operator, tracking one or more input devices (e.g., via teleoperation). In some examples, a tracking system (not shown) may be used to determine the position and orientation of display device 180 and/or the operator. In some examples, the tracking system include one or more optical fiducial sensors, optical fiducial sensors, magnetic fiducial sensors, position sensors, velocity sensors, inertial sensors (e.g., accelerometers), and/or the like to track one or more fiducial markers, a kinematic chain, and/or the like associated with display device 180 and/or the operator (e.g., when display device 180 is maintained in a fixed relative position to the operator, such as for a head-mounted and/or hand-mounted display). In some examples, the tracking system may be included as part of display device 180 or may be separate from display device 180.

In some examples, when there is a no discrepancy between an actual position and/or orientation of the imaging device and the position and/or orientation of the imaging device commanded by the operator and/or control module 160, displaying the images from the imaging device as full-screen images and/or within a static imaging window (e.g., imaging window 190) does not tend to provide confusing and/or disorienting information regarding the imaging device to the operator.

However, when the actual position and/or orientation of the imaging device is not able to closely follow the commanded position and/or orientation of the imaging device, displaying the images from the imaging device in a static way may result in confusing and/or disorienting information being provided to the operator. In some examples, the actual position and/or orientation of the imaging device may differ from the position and/or orientation as commanded by the operator (such as due to the movement of display device 180, tracking of the operator, monitoring of operator input devices used to control the imaging device, and/or like) because the imaging device is not able to move as quickly as the operator is able to command movement of the imaging device, the imaging device may reach a range of motion limit, the imaging device may have fewer degrees of freedom (DOFs) (e.g., 4—pan, tilt, roll, and insert/retract) than the mechanism used to command movement of the imaging device (e.g., 6—pan, tilt, roll, forward/back, up/down, and left/right), and/or the like. In some examples, the confusing and/or disorienting information may include providing the operator with incorrect information regarding the actual position and/or orientation of the imaging device and thus an incorrect indication of where and/or what the images the imaging device are showing. In some examples, this may result in lack of change in the images from the imaging device even though continued movement of the imaging device is being commanded, continued motion/change in the images from the imaging device as the imaging device continues to move after commands to move the imaging device have stopped, providing little or no indication that the imaging device is not able to move to accommodate the position and/or orientation being commanded, and/or the like. In some examples, the lag and/or differences in motion may also cause the operator to experience something akin to VR sickness.

In some embodiments, the problems associated with the static imaging window may be addressed by using a dynamic imaging window (e.g., imaging window 190) whose position and/or orientation changes based on tracking differences between the commanded position and/or orientation of the imaging device and the actual position and/or orientation of the imaging device. In some examples, as actual position and/or orientation of the imaging device begins to lag behind (temporally and/or spatially) the its commanded position and/or orientation (e.g., due to slower movement of the imaging device, a range of motion limit, a DOF mismatch, and/or the like), imaging module 170 may alter a position and/or orientation of imaging window 190 to indicate the lag. As an example, when the imaging device is commanded to pan left and the imaging device begins to lag behind the command, imaging window 190 may be moved to the right on display device 180 to show this. When the command to pan the imaging device to the left is complete and the imaging device is able to catch up, imaging window 190 may be moved back to the left on display device 180 to show this.

Figure 2:
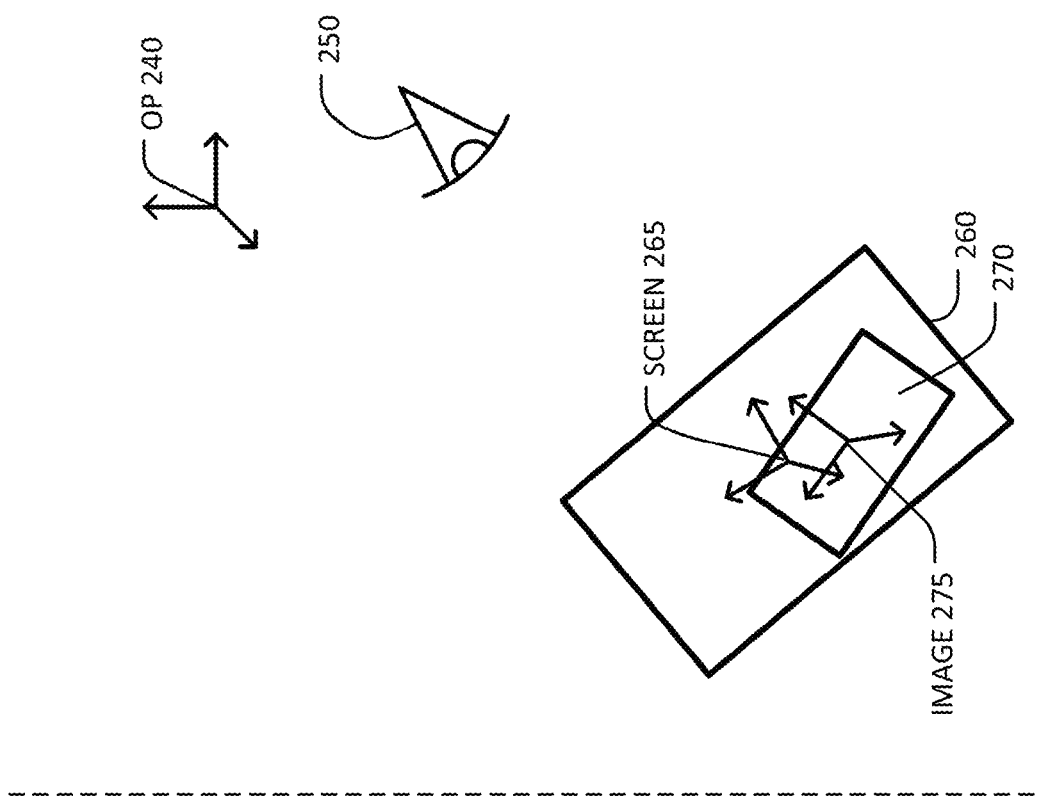
FIG. 2 is simplified diagram of an imaging and display environment according to some embodiments.
Figure 2:
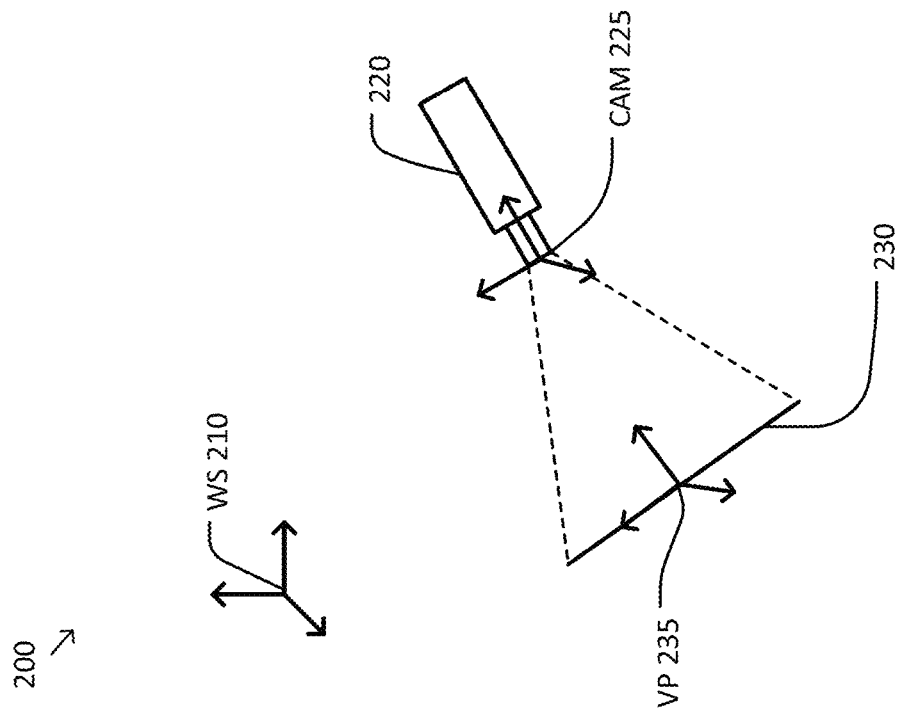

FIG. 2 is simplified diagram of an imaging and display environment 200 according to some embodiments. In some embodiments, imaging and display environment 200 corresponds to a scenario where tracking of a head-mounted and/or hand-held display device, such as display device 180 is used to provide movement commands for an imaging device. As shown in FIG. 2, imaging and display environment 200 includes a workspace coordinate system (WS) 210. In some examples, workspace coordinate system 210 corresponds to a base frame of reference for a workspace that contains a computer-assisted device, such as computer-assisted device 110. In some examples, workspace coordinate system 210 may correspond to a base of the computer-assisted device and oriented relative to the computer-assisted device, to another piece of equipment in the workspace, to an inertial reference such as the Earth, or to any other appropriate reference. In some examples, workspace coordinate system may correspond to a patient coordinate system, such as corresponding to a coordinate system statically located and oriented relative to a part of the patient, when the computer-assisted device is used to perform a procedure on a patient.

In the example of FIG. 2, an imaging device 220 is mounted near a distal end of a repositionable arm (not shown) of the computer assisted device. In some examples, imaging device 220 may be consistent with one of the one or more end effectors 125 mounted to one of the one or more repositionable arms 120. In some medical examples, imaging device 220 may be an endoscope, a camera separate from an endoscope, an ultrasonic device, a fluoroscopic device, and/or the like. In some examples, imaging device 220 may be inserted into a worksite (e.g., anatomy of a patient, a veterinary subject, and/or the like) through a cannula mounted to the repositionable arm. A camera coordinate system (CAM) 225 is associated with imaging device 220. In some examples, camera coordinate system 225 is described by a direction of view, a view up vector, and a view horizontal vector orthogonal to the direction of view and the view up vector. In some examples, the direction of view may correspond to an insertion axis of the imaging device 220, and/or may be at an angle relative to the insertion axis of the imaging device 220.

A view plane 230 is defined relative to imaging device 220 and has an associated view plane coordinate system (VP) 235. In some examples, view plane 230 may be located at a known distance from imaging device 220 along the direction of view and have view up and view horizontal vectors that correspond to the view up and view horizontal vectors, respectively, of camera coordinate system 225. In some examples, the known distance may be a user configurable distance, a distance based on a focal length of imaging device 220, a working distance from imaging device, an expected distance of a workspace from the imaging device, and/or the like. In some examples, view plane coordinate system 235 may be located at a center point of view plane 230.

In some embodiments, Equation 1 may be used to describe the relationships between workspace coordinate system 210, camera coordinate system 225, and view plane coordinate system 235, where $^{A}T_{B}$ represents a coordinate transform (e.g., a homogenous transform) from coordinate system A to coordinate system B (e.g., a position and orientation of coordinate system B in coordinate system A). In some examples, $^{WS}T_{CAM}$ may be determined by tracking a kinematic chain of the computer-assisted device and the repositionable arm to which imaging device 220 is mounted (e.g., by using information from one or more joint sensors of the computer-assisted device and the repositionable arm and applying one or more kinematic models of the computer-assisted device and the repositionable arm). In some examples, $^{CAM}T_{vp}$ may be determined based on the defined relationship between imaging device 220/camera coordinate system 225 and view plane 230/view plane coordinate system 235.

$$^{WS}T_{VP} = {}^{WS}T_{CAM}{}^{CAM}T_{VP} \qquad \text{Equation 1}$$

Imaging and display environment 200 further includes an operator coordinate system (OP) 240. In some examples, operator coordinate system 240 corresponds to a base frame of reference for an operator. In some examples, operator coordinate system 240 may correspond to a base and/or other portion of an operator console (not shown), a base of an operator input device, a location and orientation of the operator, an inertial frame of reference, and/or the like.

An operator point of view 250 is used to indicate a location and direction of view of the operator. In some examples, operator point of view 250 may correspond to an eye and/or an approximation of both eyes of the operator. In some examples, operator coordinate system 240 may be located and/or oriented based on the operator point of view 250.

A display device 260 is located within operator coordinate system 240. In some examples, display device 260 may be consistent with display device 180. In some examples, display device 260 may be a repositionable display device, such as a tablet, a smart phone, a head-mounted display, and/or the like. A screen coordinate system (SCREEN) 265 is associated with display device 260. In some examples, screen coordinate system 265 may be positioned at a center point of display device 260. In some examples, screen coordinate system 265 may be oriented based on horizontal and vertical axes and a view out vector of display device 260. In some examples, the relationship (e.g., transform) locating screen coordinate system 265 relative to operator coordinate system 240 may be determined based on tracking of display device 260 similar to the tracking of display device 180.

An imaging window 270 is displayed on display device 260. In some examples, imaging window 270 may be consistent with imaging window 190. An imaging coordinate system (IMAGE) 275 is associated with imaging window 270. In some examples, imaging coordinate system 275 may be positioned at a center point of imaging window 270. In some examples, imaging coordinate system 275 may be oriented based on horizontal and vertical axes of images being displayed and a view out vector of the display screen of display device 260. In some examples, where display device 260 supports three-dimensional viewing (e.g., display device 260 is a stereoscopic display) the view out vector may correspond to a direction from which the displayed image is captured relative to a plane defined by the horizontal and vertical axes. In some examples, an angular width of imaging window 270 may be determined based on an angular width of the field of view of imaging device 220 to help reduce issues associated with aspect ratio problems, misleading motion cues, and/or the like.

In some embodiments, Equation 2 may be used to describe the relationships between operator coordinate system 240, screen coordinate system 265 and imaging coordinate system 275. In some examples, $^{OP}T_{SCREEN}$ may be determined by tracking display device 260 as it moves within operator coordinate system 240.

$$^{OP}T_{IMAGE} = {^{OP}T_{SCREEN}} \, ^{SCREEN}T_{IMAGE} \qquad \text{Equation 2}$$

In some embodiments, in order to support intuitive control of the computer-assisted device, it is helpful to render images received from imaging device 220 on display device 260 (e.g., in imaging window 270) at a position and orientation relative to operator point of view 250 that is consistent with the location of view plane 230 within workspace coordinate system 210. In some examples, the consistency in the display of the images may be obtained by equating the transform $^{WS}T_{vp}$ between workspace coordinate system 210 and view plane coordinate system 235 as equivalent to the transform $^{OP}T_{IMAGE}$ between operator coordinate system 240 and imaging coordinate system 275.

As described previously with respect to Equation 1, $^{WS}T_{vp}$, may be determined from the actual position and orientation of imaging device 220 (e.g., from the kinematic chain of the computer-assisted device) and the relationship between imaging device 220 and view plane 230. Further, as described previously with respect to Equation 2, $^{OP}T_{SCREEN}$ may be determined by tracking display device 260 within operator coordinate system 240. Thus, Equation 3 may be used to determine $^{SCREEN}T_{IMAGE}$, which may also be used to position and orient imaging window 270 (and thus the images from imaging device 220 being rendered) relative to display device 260. Thus, when the movement of imaging device 220 does not lag from the movement commanded by movement of display device 260, $^{SCREEN}T_{IMAGE}$ is a unity transform and imaging window 270 and the images being rendered are displayed centered on display device 260 and aligned with display device 260. However, when imaging device 220 begins to lag (e.g., due to a slower motion, range of motion limits, DOF mismatches, and/or the like) the actual position and orientation of imaging device 220, as captured by $^{SCREEN}T_{IMAGE}$, results in a non-unity transform for $^{SCREEN}T_{IMAGE}$ so that imaging window 270 and the rendered images are adjusted to reflect the lag in movement of imaging device 220.

$$^{SCREEN}T_{IMAGE} = \left(^{OP}T_{SCREEN}\right)^{-1} \, ^{OP}T_{IMAGE} \qquad \text{Equation 3}$$

As discussed above and further emphasized here, FIG. 2 is merely an example which should not unduly limit the scope of the claims. One of ordinary skill in the art would recognize many variations, alternatives, and modifications. According to some embodiments, Equations 1-3 may be altered so as to conceal tracking issues associated with the imaging device that the operator cannot address. In some examples, Equations 1-3 may be altered to remove discrepancies caused by degree of freedom differences between the mechanism used to command the imaging device and actual degrees of freedom of the display device (e.g., discrepancies due to commanding a 4 DOF display device with a 6 DOF control mechanism) while still addressing discrepancies from other sources (such as range of motion limits, lag, and/or the like).

In some embodiments, where position and/or orientation of the imaging device is not controlled by movement of the display device and/or some sources of discrepancy are to be removed from the position and/or orientation of the imaging window other computations may be used. In some examples, when the position and/or orientation of the imaging device is not controlled by movement of the display device, the $^{SCREEN}T_{IMAGE}$ transform may be determined according to Equation 4, where the transform is based on differences between the actual position and orientation of the imaging device and the commanded position and orientation of the imaging device, where the actual position and orientation are determined using the actual position and orientation of the kinematic chain used to control the imaging device.

$$^{SCREEN}T_{IMAGE} = {^{CommandPOS}T_{ActualPOS}} \qquad \text{Equation 4}$$

In some examples, control of whether to remove discrepancies due to lag and/or range of motion and degree of freedom differences may be addressed by using a virtual slave estimation of the position and orientation of the imaging device. In some examples, the commanded position and/or orientation for the imaging device, which is based on the input command provided by, for example, the operator, may not be completely obtainable by the kinematic chain used to control the imaging device (e.g., due to differences in degrees of freedom, range of motion limits, collisions, and/or the like). The virtual slave estimation of the position and/or orientation of the imaging device may be determined from the commanded position and/or orientation for the imaging device using the inverse kinematics of the kinematic chain used to control the imaging device as an indicator of a closest reasonable position and/or orientation of the imaging device subject to the practical limitations of differences in degrees of freedom, range of motion limits, collisions, and/or the like. In some examples, when the imaging window is to be positioned and oriented to address only discrepancies due to lag in the ability of the imaging device to keep up with the commanded position and orientation and not discrepancies due to range of motion limits and degree of freedom differences, Equation 6 may be used. In some examples, when the imaging window is to be positioned and oriented to address only discrepancies due to range of motion limits and degree of freedom differences and not discrepancies due to lag in the ability of the imaging device to keep up with the commanded position and orientation, Equation 5 may be used, where the actual position and orientation of the imaging device may be determined from the forward kinematics of the kinematic chain used to control the imaging device.

$$^{SCREEN}T_{IMAGE} = {}^{CommandPOS}T_{VirtualSlave} \qquad \text{Equation 5}$$

$$^{SCREEN}T_{IMAGE} = {}^{VirtualSlave}T_{ActualPOS} \qquad \text{Equation 6}$$

Figure 3:
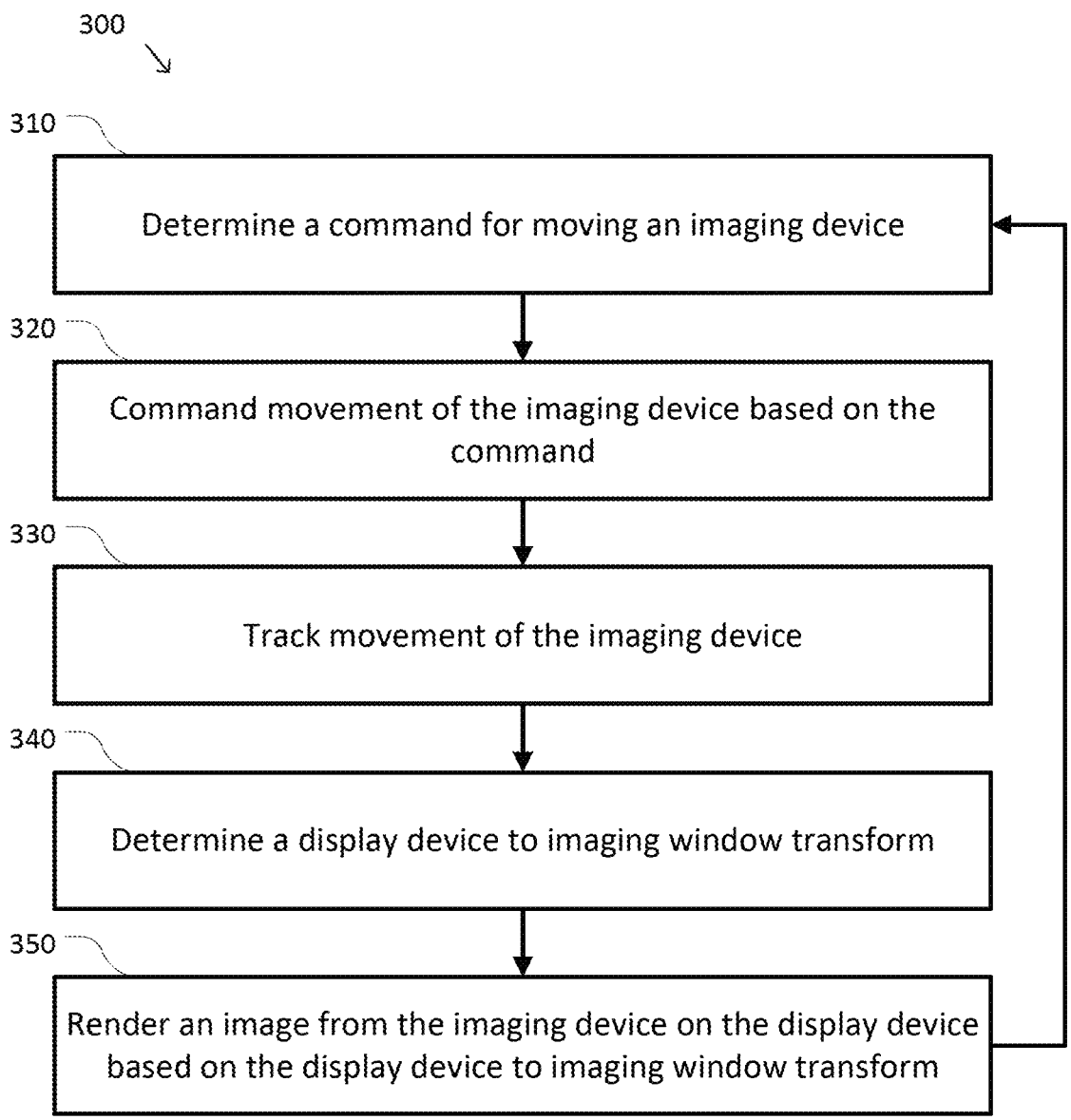
FIG. 3 is a simplified diagram of a method of displaying images from an imaging device according to some embodiments.

FIG. 3 is a simplified diagram of a method 300 of displaying images from an imaging device according to some embodiments. One or more of the processes 310-350 of method 300 may be implemented, at least in part, in the form of executable code stored on non-transitory, tangible, machine-readable media that when run by one or more processors (e.g., the processor 140 in control unit 130) may cause the one or more processors to perform one or more of the processes 310-350. In some embodiments, method 300 may be performed by one or more modules, such as control module 160 and/or imaging module 170. In some embodiments, method 300 may be used to render images from an imaging device (e.g., imaging device 220) on a display device (e.g., display device 180 and/or 260) in an imaging window (e.g., imaging window 190 and/or 270) so as to provide visual cues to an operator when the imaging device is not able to match movement commands caused by movement of the display device. In some embodiments, method 300 may be used to reduce something akin to VR sickness in an operator using the display device to teleoperate the imaging device. In some embodiments, method 300 may allow an operator to provide rapid movement commands to an imaging device without having to wait for the imaging device to complete the movement commands while still providing cues to the operator regarding the completion status of the movement commands.

At a process 310, a command for an imaging device is determined. In some examples, when the imaging device is controlled via movement of the display device (e.g., the display device is head-mounted, hand-held, and/or the like), the command may be determined based on the movement of the display device. In some examples, the command may be determined by tracking movement of the operator (e.g., motion of one or more hands of the operator), monitoring one or more operator input devices, and/or the like. In some examples, the movement of the display device and/or movement of the operator may be detected using a tracking system, such as the tracking system described with respect to FIGS. 1 and 2.

At a process 320, an imaging device is teleoperated based on the command. In some examples, when the imaging device is controlled via movement of the display device, changes in position and/or orientation of the display device may be used to make a corresponding change in position and/or orientation of the imaging device. As an example, when the display device is moved upward, a field of view of the imaging device is moved upward via a corresponding upward movement of the imaging device. As another example, when the display device is moved along a leftward arc (e.g., due to rotation of a torso of the operator, rotation of a head of the operator for a head mounted display, and/or the like), the imaging device may be panned to the left causing a corresponding change in the field of view of the imaging device. In some examples, the imaging device may be moved by sending one or more signals to one or more actuators associated with joints of a computer-assisted device (e.g., computer-assisted device 110) and a repositionable arm (e.g., one of the one or more repositionable arms 120) to which the imaging device is mounted.

At a process 330, movement of the imaging device is tracked. In some examples, movement of the imaging device may be tracked by tracking a kinematic chain of the computer-assisted device and the repositionable arm to which the imaging device 220 is mounted. In some examples, information from one or more joint sensors of the computer-assisted device and the repositionable arm and one or more kinematic models of the computer-assisted device and the repositionable arm may be used to track the kinematic chain. In some examples, the tracked movement of the imaging device may provide an actual position and/or orientation of the imaging device in a workspace coordinate system, such as workspace coordinate system 210. In some examples, the inverse kinematics of the kinematic chain may be used to determine the virtual slave position and/or orientation of the imaging device.

At a process 340, a display device to imaging window transform is determined. In some examples, when the imaging device is controlled via movement of the display device, the display device to imaging window transform may be determined according to FIG. 2 and Equations 1-3. In some examples, the display device to imaging window transform may alternatively be determined based on any one of Equations 4-6. In some examples, the display device to imaging window transform may describe differences between a position and/or orientation of the imaging device determined by the movement of the display device and an actual position and orientation of the imaging device.

At a process 350, an image from the imaging device is rendered on the display device based on the display device to imaging window transform. In some examples, the image is displayed in an imaging window, such as imaging window 190 and/or 270) at a position and orientation on a display screen of the display device according to the display device to imaging window transform. In some examples, the image may be projected onto the imaging window. In some examples, the position and orientation of the image and the imaging window on the display screen may provide visual cues to the operator when the imaging device is not able to follow its commanded movement determined during process 310. In some examples, rendering the image from the imaging device on the display device based on the display device to imaging window transform may provide one or more visual cues regarding an inability of the imaging device to track the commanded movement of the imaging device due to lag in the movement of the imaging device, a range of motion limit of the imaging device, issues associated with a degree-of-freedom differences between the imaging device and the display device, and/or the like.

Upon completion of process 350, method 300 may repeat processes 310-350 to detect further movement of the display device, teleoperate the imaging device accordingly, and render additional images from the imaging device in a dynamically positioned and oriented imaging window on the display device.

Figure 4:
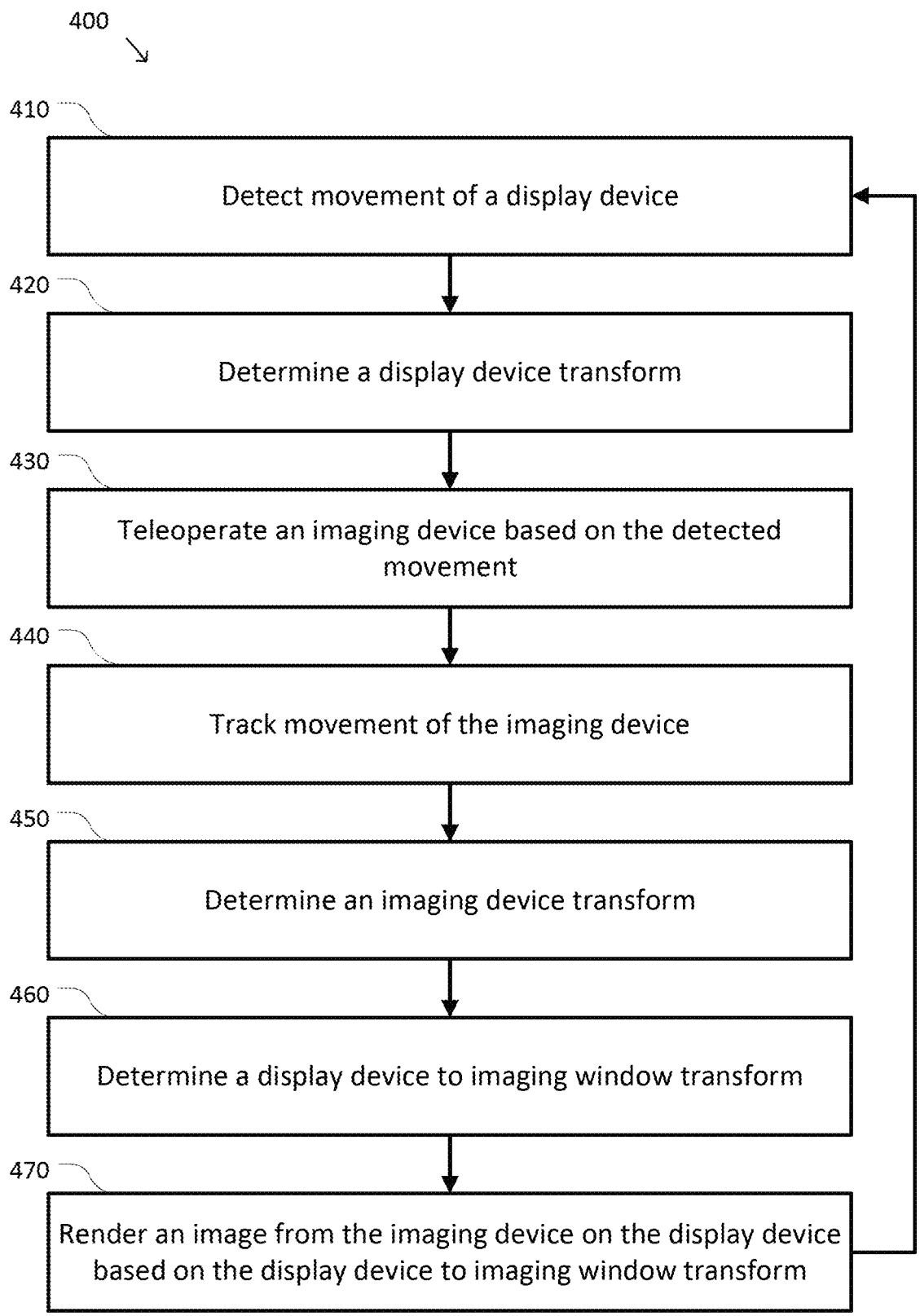
FIG. 4 is a simplified diagram of a method of displaying images from an imaging device according to some embodiments.

FIG. 4 is a simplified diagram of a method 400 of displaying images from an imaging device according to some embodiments. In some embodiments, method 400 is consistent with method 300. One or more of the processes 410-470 of method 400 may be implemented, at least in part, in the form of executable code stored on non-transitory, tangible, machine-readable media that when run by one or more processors (e.g., the processor 140 in control unit 130) may cause the one or more processors to perform one or more of the processes 410-470. In some embodiments, method 400 may be performed by a module, such as imaging module 160. In some embodiments, method 400 may be used to render images from an imaging device (e.g., imaging device 220) on a display device (e.g., display device 180 and/or 260) in an imaging window (e.g., imaging window 190 and/or 270) so as to provide visual cues to an operator when the imaging device is not able to match movement commands caused by movement of the display device. In some embodiments, method 400 may be used to reduce something akin to VR sickness in an operator using the display device to teleoperate the imaging device. In some embodiments, method 400 may allow an operator to provide rapid movement commands to an imaging device without having to wait for the imaging device to complete the movement commands while still providing cues to the operator regarding the completion status of the movement commands.

At a process 410, movement of a display device is detected. In some examples, the movement of the display device may be detected using a tracking system, such as the tracking system described with respect to FIGS. 1 and 2. In some examples, the tracking system may track one or more fiducial markers, a kinematic chain, one or more inertial sensors (e.g., accelerometers), and/or the like associated with the display device and/or an operator (e.g., when the display device is maintained in a fixed relative position to the operator, such as for a head-mounted display). In some examples, the tracking system may be included as part of the display device and/or separate from the display device. In some examples, the movement detected may include changes in position, orientation, or both position and orientation of the display device.

At a process 420, a display device transform is determined. In some examples, the display device transform may be determined relative to an operator coordinate system, such as operator coordinate system 240. In some examples, the display device transform may correspond to the transform $^{OP}T_{SCREEN}$ and be determined as described with respect to FIG. 2.

At a process 430, an imaging device is teleoperated based on the detected movement of the display device. In some examples, process 430 may be substantially similar to process 320 where the command is determined based on the detected movement of the display device.

At a process 440, movement of the imaging device is tracked. In some examples, process 440 may be substantially similar to process 330.

At a process 450, an imaging device transform is determined. In some examples, the imaging device transform may correspond to a transform between the workspace coordinate system to a view plane coordinate system associated with the imaging device. In some examples, the imaging device transform may correspond to $^{WS}T_{vp}$ as described with respect to FIG. 2. In some examples, the imaging device transform may be determined by combining information associated with the tracked movement of the imaging device from process 440 combined with information describing the relationship between the imaging device and a representative view plane for the imaging device. In some examples, Equation 1 may be used to determine the imaging device transform.

At a process 460, a display device to imaging window transform is determined. In some examples, the display device to imaging window transform may be determined based on the display device transform determined during process 420 and the imaging device transform determined during process 450. In some examples, the display device to imaging window transform may correspond to $^{SCREEN}T_{IMAGE}$ as described with respect to FIG. 2. In some examples, the display device to imaging window transform may be determined according to Equation 3. In some examples, the display device to imaging window transform may describe differences between a position and/or orientation of the imaging device determined by the movement of the display device and an actual position and orientation of the imaging device.

At a process 470, an image from the imaging device is rendered on the display device based on the display device to imaging window transform. In some examples, process 470 may be substantially similar to process 350.

Upon completion of process 470, method 400 may repeat processes 410-470 to detect further movement of the display device, teleoperate the imaging device accordingly, and render additional images from the imaging device in a dynamically positioned and oriented imaging window on the display device.

As discussed above and further emphasized here, FIGS. 3 and 4 are merely an example which should not unduly limit the scope of the claims. One of ordinary skill in the art would recognize many variations, alternatives, and modifications. According to some embodiments, methods 300 and/or 400 may be adapted to handle a stereoscopic imaging device and a stereoscopic display device. In some examples, the stereoscopic imaging device may correspond to a stereoscopic endoscope and/or the like capturing left and right images. In some examples, the stereoscopic display device may correspond to a pair of head-mounted VR or AR goggles and/or the like displaying left and right images on left and right display devices. In some examples, processes 340, 350, 460, and/or 470 may include dual sub-processes for determining separate left and right display device to imaging window transforms. In some examples, the separate left and right display device to imaging window transforms may be used to separately render left images from the stereoscopic imaging device in a left imaging window on the left display device and right images from the stereoscopic imaging device in a right imaging window on the right display device. In some examples, separate left and right transforms are not used, but separate left and right images are rendered.

Some examples of control units, such as control unit 130 may include non-transitory, tangible, machine readable media that include executable code that when run by one or more processors (e.g., processor 140) may cause the one or more processors to perform the processes of methods 300 and/or 400. Some common forms of machine readable media that may include the processes of methods 300 and/or 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device comprising:
a display device; and
one or more processors coupled to the display device, the one or more processors being configured to:
track movement of an imaging device;
determine a display-device-to-imaging-window transform based on the tracked movement of the imaging device; and
display an image from the imaging device on the display device, a position and an orientation of the image on the display device being based on the display-device-to-imaging-window transform;
wherein the position and the orientation of the image on the display device provides one or more cues to an operator regarding at least one of:
an inability of the imaging device to follow a command to move the imaging device,
a range of motion limit of the imaging device, or
a mismatch in degrees of freedom between the imaging device and the display device.

2. The computer-assisted device of claim 1, wherein the one or more processors are further configured to:
position an imaging window on the display device, a position and an orientation of the imaging window being based on the display-device-to-imaging-window transform; and
render the image in the imaging window.

3. The computer-assisted device of claim 2, wherein the one or more processors are further configured to:
project the image onto the imaging window.

4. The computer-assisted device of claim 1, wherein to determine the display-device-to-imaging-window transform, the one or more processors are configured to determine at least one of:
a difference between an actual position of the imaging device and a position of the imaging device indicated by the command; or
a difference between an actual orientation of the imaging device and an orientation of the imaging device indicated by the command.

5. The computer-assisted device of claim 1, wherein the one or more processors are further configured to:
determine the command to move the imaging device based on detected motion of the display device.

6. The computer-assisted device of claim 5, wherein to determine the display-device-to-imaging-window transform, the one or processors are configured to determine a display device transform based on the detected motion of the display device.

7. The computer-assisted device of claim 5, further comprising:
a tracking system comprising a sensor selected from the group consisting of: an optical fiducial sensor, a magnetic fiducial sensor, an inertial sensor, a position sensor configured to provide position information of a kinematic chain associated with the display device, and a velocity sensor configured to provide velocity information of the kinematic chain;
wherein the one or more processors are further configured to:
use the tracking system to acquire the detected motion of the display device.

8. The computer-assisted device of claim 1, wherein to determine the display-device-to-imaging-window transform, the one or more processors are configured to determine an imaging device transform based on a position and an orientation of a view plane of the imaging device.

9. The computer-assisted device of claim 1, wherein the one or more processors are further configured to:
determine a display device transform based on detected movement of the display device;
determine an imaging device transform based on the tracked movement of the imaging device; and
determine the display-device-to-imaging-window transform based on the display device transform and the imaging device transform.

10. The computer-assisted device of claim 1, wherein a direction of view of the imaging device is at an angle relative to an insertion axis of the imaging device into a workspace.

11. The computer-assisted device of claim 1, wherein the display device comprises a tablet, a smart phone, or a head-mounted display.

12. The computer-assisted device of claim 1, wherein:
the display device is a stereoscopic device; and
the imaging device is a stereoscopic device; and
to display the image from the imaging device, the one or more processors are configured to display left and right images received from the imaging device.

13. The computer-assisted device of claim 1, wherein:
the display device has six degrees of freedom; and
the imaging device has four degrees of freedom.

14. A method comprising:
tracking, by a control unit of a computer-assisted device, movement of an imaging device;
determining, by the control unit, a display-device-to-imaging-window transform based on the tracked movement of the imaging device; and
displaying, by the control unit, an image captured by the imaging device on a display device, a position and an orientation of the image on the display device being based on the display-device-to-imaging-window transform;
wherein the position and the orientation of the image on the display device provides one or more cues to an operator regarding at least one of:
an inability of the imaging device to follow a command to move the imaging device,
a range of motion limit of the imaging device, or
a mismatch in degrees of freedom between the imaging device and the display device.

15. The method of claim 14, further comprising:
positioning, by the control unit, an imaging window on the display device, a position and an orientation of the imaging window being based on the display-device-to-imaging-window transform; and
rendering, by the control unit, the image in the imaging window.

16. The method of claim 15, further comprising:
projecting, by the control unit, the image onto the imaging window.

17. The method of claim 14, wherein determining the display-device-to-imaging-window transform comprises at least one of:
determining a difference between an actual position of the imaging device and a position of the imaging device indicated by the command; or
determining a difference between an actual orientation of the imaging device and an orientation of the imaging device indicated by the command.

18. The method of claim 14, further comprising:
determining, by the control unit, the command to move the imaging device based on detected motion of the display device.

19. The method of claim 14, further comprising:
determining, by the control unit, a display device transform based on detected movement of the display device;
determining, by the control unit, an imaging device transform based on the tracked movement of the imaging device; and
determining, by the control unit, the display-device-to-imaging-window transform based on the display device transform and the imaging device transform.

20. A non-transitory machine-readable medium comprising a plurality of machine-readable instructions which when executed by one or more processors are adapted to cause the one or more processors to perform a method comprising:
tracking movement of an imaging device;
determining a display-device-to-imaging-window transform based on the tracked movement of the imaging device; and
displaying an image captured by the imaging device on a display device, a position and an orientation of the image on the display device being based on the display-device-to-imaging-window transform;
wherein the position and the orientation of the image on the display device provides one or more cues to an operator regarding at least one of:
an inability of the imaging device to follow a command to move the imaging device,
a range of motion limit of the imaging device, or
a mismatch in degrees of freedom between the imaging device and the display device.

* * * * *

UNITED STATES PATENT AND TRADEMARK OFFICE
CERTIFICATE OF CORRECTION

| | | Page 1 of 1 |
|---|---|---|
| PATENT NO. | : 12,419,698 B2 | |
| APPLICATION NO. | : 18/646112 | |
| DATED | : September 23, 2025 | |
| INVENTOR(S) | : Gabriel F. Brisson | |

It is certified that error appears in the above-identified patent and that said Letters Patent is hereby corrected as shown below:

On the Title Page

Item [63], Please delete "Continuation of application No. 17/265,486, filed as application No. PCT/US2019/044852 on Aug. 2, 2019, now Pat. No. 11,992,273." and insert --Continuation of application No. 17/265,486, filed on Feb. 2, 2021, now Pat. No. 11,992,273, which is a 371 of application No. PCT/US2019/044852, filed on Aug. 2, 2019.--.

Signed and Sealed this
Twenty-eighth Day of October, 2025

John A. Squires
*Director of the United States Patent and Trademark Office*